US006898594B2

(12) United States Patent
Ushijima et al.

(10) Patent No.: US 6,898,594 B2
(45) Date of Patent: May 24, 2005

(54) INTEGRATED DATABASE SYSTEM AND PROGRAM STORAGE MEDIUM

(75) Inventors: Kazutomo Ushijima, Kokubunji (JP);
Itaru Nishizawa, Koganei (JP);
Takahiko Shintani, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 247 days.

(21) Appl. No.: 09/932,114

(22) Filed: Aug. 20, 2001

(65) Prior Publication Data

US 2002/0120618 A1 Aug. 29, 2002

(30) Foreign Application Priority Data

Feb. 28, 2001 (JP) ...................................... 2001-053474

(51) Int. Cl.$^7$ .............................................. G06F 17/30
(52) U.S. Cl. ................................. 707/5; 707/4; 707/10
(58) Field of Search .................................. 707/1–6, 10

(56) References Cited

U.S. PATENT DOCUMENTS

| | | | |
|---|---|---|---|
| 5,588,150 A | | 12/1996 | Lin et al. |
| 5,590,319 A | * | 12/1996 | Cohen et al. ................... 707/4 |
| 6,092,062 A | * | 7/2000 | Lohman et al. ................ 707/2 |
| 6,279,030 B1 | * | 8/2001 | Britton et al. ............... 709/203 |
| 6,353,818 B1 | * | 3/2002 | Carino, Jr. ..................... 707/2 |
| 6,546,381 B1 | * | 4/2003 | Subramanian et al. ......... 707/2 |
| 6,651,072 B1 | * | 11/2003 | Carino et al. ................. 707/10 |
| 2001/0051949 A1 | * | 12/2001 | Carey et al. | |

OTHER PUBLICATIONS

Chen Li et al, "Capability Based Mediation in TSIMMIS", described at pp. 564–566 in "ACM SIGMOD International Conference on Management of Data(SIGMOD'98)" issued by ACM Press, 1998.
"Foundations of Intelligent Knowledge–Based Systems" issued by Academic Press, Chapter 12, 1995.
JP–A–11–85522.
C.A. Goble et al, "Transparent Access to Multiple Bioinformatics Information Sources", IBM Systems Journal, vol. 40, No. 2, pp. 532–551, 2001.
JP–A–2001–109758.

* cited by examiner

*Primary Examiner*—Greta Robinson
*Assistant Examiner*—Debbie M. Le
(74) *Attorney, Agent, or Firm*—Mattingly, Stanger, Malur & Brundidge, P.C.

(57) ABSTRACT

By corresponding the external databases to the predicates used in query processing according to a predetermined ontology, it is allowed to issue a query through the ontology. The query thrown into the integrated database is expanded into the set of approximate queries according to approximation rules provided in the ontology. The optimization module refers to the query capability of the external databases to perform the query optimizing in which these approximate queries can be executed efficiently as a whole.

11 Claims, 11 Drawing Sheets

FIG.9
SCHEMATIC DIAGRAM SHOWING A BIOMOLECULAR RELATION CORRESPONDING TO APPROXIMATION RULES

FIG.10

INTEGRATED DATABASE SYSTEM AND PROGRAM STORAGE MEDIUM

BACKGROUND OF THE INVENTION

1. Field of the Invention

The present invention relates to an integrated database system that integrates databases and arbitrary data sources, such as database and web servers which are connected via networks, to perform the query processing. More particularly, the present invention relates to a system that optimizes a query issued to an integrated database.

2. Description of the Related Art

The Human Genome Project, which was initiated in 1990 in an effort to obtain all human DNA sequence data in about 15 years, published in June 2000 the draft sequences accounting for about 85% of all human genomes, due to the accelerated sequencing speed realized by the rapid advance of the sequencing technology and by the application of the large-scale rearrangement method (shotgun cloning) using the parallel computers. In parallel with the Human Genome Project, other projects are also under way to map the DNA sequence data from various biological species other than humans. These projects have accumulated in the individual databases (bio-information databases) in an orderly manner decoded data on the amino acid sequences and the three-dimensional structures of protein in living organisms and data on metabolic pathways. These databases are in many cases managed by the public organizations, and can be accessed their contents by issuing a query via the Internet.

A variety of analysis tools extracting information obtained by deriving from the sequence data (for example, by estimating a gene coding area from a large volume of DNA sequence data, or by estimating the three-dimensional structure of protein) are being proposed one after another. Some of these tools are made public in the form available on the Internet.

The methods for obtaining the experimental data in the laboratories have also undergone drastic changes. The techniques to retrieve a large amount of data with high throughput have been devised, including the DNA micro-array method capable of measuring the abundance (or representation) of many genes in individual cells simultaneously. With the new developments in the measuring process, a huge volume of experimental results are being stored in the laboratories. Under these circumstances, it is important from now on to utilize a wide range of databases and tools in combination to understand what roles the genes and proteins encoded in the sequence data play in living organisms and in what way they are related to each other, and to apply findings to the fields of medicine manufacturing, medical care and foods.

For the understanding of the complex biological phenomena, it is essential to perform the query processing combining these databases and tools to analyze the retrieved data. This, however, is accompanied by the following difficulties.

(1) The formats or structures of data stored in the databases differ from one database to another, and these databases also have no unified form of the executable query. It is therefore difficult to easily issue a query that simultaneously combines the databases to use the combined databases.

(2) Since the different databases have the different query capabilities as to the data coverage and the description level of data stored in the databases, it is difficult to decide which databases should properly be linked and queried.

With the advance of technology, the number of new databases and tools that can be used in combination is rapidly increasing. However, since they are individually maintained and made available for public access, the above two aspects are not taken into consideration, and it takes an enormous amount of time and labor to use the new databases in integration with the existing ones.

For the efficient analysis of bio-information, it is therefore important to build an integrated database system that can easily issue a query capable of using a plurality of directly irrelevant databases and tools in combination, and can execute such a query efficiently.

In order to perform the efficient query processing in the integrated database system that integrates a plurality of databases, it is important to realize the query optimization mechanism that provides the integrated interface for cross-linking a plurality of external databases having different data formats, and converts the issued query into the efficient query plan to execute the query plan.

There are two following schemes as the conventional query optimization scheme in the integrated database system. That is, as the first scheme, there is the approach in the wrapper mediator system disclosed in "Capability Based Mediation In TSIMMIS" in "ACM SIGMOD International Conference On Management of Data (SIGMOD' 98)" (published by ACM Press), p.564–566, and in U.S. Pat. No. 5,588,150. As the second scheme, there is the approach in the multiagent system disclosed in "Multiagent Systems" in Chapter 12 of "Foundations of Intelligent Knowledge-Based Systems" (published by Academic Press) and in JP-A-11-85522.

In the wrapper mediator type integrated database system according to the first conventional scheme, the individual external databases are provided with the programs (called the wrappers) for transforming the query and data format into acceptable ones to the databases. The mediator combines the appropriate wrappers and provides a unified query interface to the wrappers. Thereby, the user can access a plurality of databases through a single interface. Here, each of the wrappers declares the query class acceptable to the wrapper itself, and registers it with the mediator. When a part or the whole part of the thrown-in query is included in the query class declared by the wrapper, the processing of that part of the query can be entrusted to the wrapper. The mediator determines whether or not it entrusts the query processing to the wrapper, based on the estimating cost of the query processing on the wrapper side and so forth.

Generally, there can be considered many alternative query plans for processing the query, which is thrown into the integrated database system, using the external databases, in terms of the combination of the external databases to be used and the order of queries. These query plans have different characteristics as to the execution cost and the data contents obtained as the query results. In the first conventional scheme, since one of the query plans for processing the thrown-in query using the external databases is selected to be executed, there is a possibility that the query results obtained may be fewer than ones that can originally be obtained using the external databases.

For example, when it is attempted to collect a set of all genes contained in human genomes using the databases currently made public, the following query methods (1) to (3) can be conceived, and the contents of the query results greatly differ.

(1) Selecting the genes, which are clearly shown to be human's ones, from the gene data registered in the gene database;

(2) Extracting by applying the gene estimation tool to the human genome data registered in the sequence database; and (3) Finding the description portions concerning the desired gene from the documents registered in the document databases to determine the target data based on the name of the gene referred to in the description portions.

Therefore, the query optimization scheme according to the first conventional scheme is not appropriate as the integrated database query optimization scheme in the field of bio-information where many databases overlap one another in terms of the stored data and the query capability, and where there are many different ways of combining the databases.

The multi-agent type integrated database system according to the second conventional scheme comprises: the external agents each of which capsules the individual data sources and the query capabilities for the data sources; and the coordinate agent for accepting the thrown-in query to forward it to the external agents. Each of the external agents registers in the coordinate agent in advance the query class that the external agent itself can be handled. For the query issued from the user, the coordinate agent trusts the query processing to the appropriate agent that can handle the query, according to the registration contents registered by the external agents. Here, the coordinate agent may transform the query and the data format so that the associated external agent can process the query, as required.

As described above, the second conventional scheme differs from the first conventional scheme in that any single interface is not provided to the user. But, it is possible to issue the query with relatively easy by having the coordinate agent conceal the difference in the data format and/or the difference in the query capability of the individual data sources.

However, in the second conventional scheme, one combination set of the destination agents for the thrown-in query is also determined according to the inclusion relation of the query processing capabilities of the agents to be executed. Hence, as the first conventional scheme, there is a possibility that the query results obtained are fewer than ones that can originally be obtained using the available external databases. For this reason, this scheme is not appropriate as the integrated database query optimization scheme in the bio-information field.

In the conventional schemes described above, the thrown-in query is executed by selecting one of some query plans for combining and executing the query processing in the external databases. Therefore, there is a possibility that the query results obtained by executing the selected query plan may be fewer than ones that can originally be obtained using the external databases.

SUMMARY OF THE INVENTION

An object of the present invention is to provide, in the integrated database system, a query optimization scheme for generating a query plan with which the query processing in the integrated database can efficiently be performed while taking into consideration the accuracy required of the query results and the cost of the query processing, when the query plan for combining and using the external databases for a query thrown in by a user is generated.

A system according to a representative aspect of the present invention is an integrated database system for integrating a plurality of external databases to perform query processing, the integrated database system comprising:

an ontology with weights for representing connections among predicates used in descriptions of a query;

specification descriptions concerning query processing capabilities of the external databases;

query expansion means for referring to the ontology to convert a query thrown into the integrated database system, into one or more query sets;

query extraction means for referring to the specification descriptions to extract queries, which can be executed using the external databases, from the converted query sets;

query selection means for referring to the weights, which are set in the ontology, to select an appropriate combination of queries from a set of the extracted queries; and query plan merging means for merging the queries in a set of the selected queries to generate a query plan.

That is, in the present invention, the query plans for processing the thrown-in query by combining the external databases are generated. The query approximation level as the measure indicating how reliable the query results to be returned for the thrown-in query is derived from the weights attached to the ontology. The query approximation level is referred to select the subset of the appropriate query plans. The query plans are merged while performing the query optimization (for example, the binding of the common-processing parts) for the thrown-in query. This can minimize the cost of the query processing, and can generate the query plan that can retrieve as many query results as possible for the thrown-in query.

A program storage medium according to the present invention is a program storage medium for storing a program that realizes an integrated database system for performing query processing by integrating a plurality of external databases, the program storage medium storing:

a predicate dictionary including information on connections among predicates used in the query processing and on strengths of the connections; and a program for realizing query expansion processing that refers to the predicate dictionary to convert a query thrown into the integrated database system, into one or more query sets.

Other aspects of the present invention and the more specific system configurations to realize these will become apparent in the following description of embodiments.

DETAILED DESCRIPTION OF THE EMBODIMENTS

Figure 1:
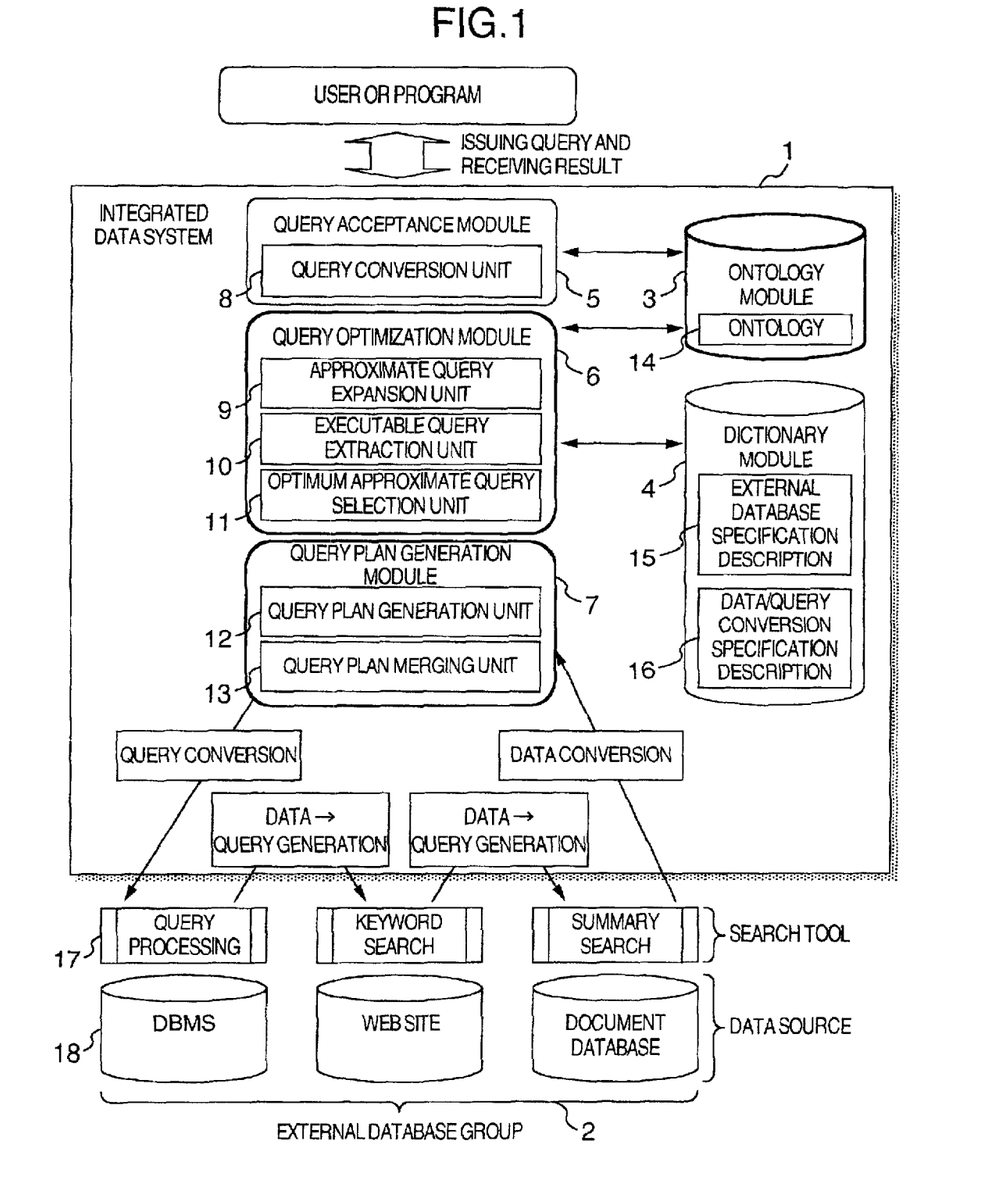
FIG. 1 is a block diagram showing an integrated database system according to an embodiment of the present invention.

FIG. 1 shows one embodiment of an integrated database system according to a query optimization scheme of the present invention.

An integrated database system 1 according to this embodiment accepts a query issued by a user or program. The integrated database system 1 generates a plurality of approximate queries which approximate the result of the query, by combining query processings on a group of external databases 2 specified in advance while referring to specifications on the accuracy of the query result and the query cost, which are specified when or before the query is thrown. The query plans of these approximate queries are merged to generate a query plan that more efficiently approximates the thrown-in query. The integrated database system 1 returns to the user or program the execution result of this query plan as the approximated query result of the original thrown-in query.

In FIG. 1, an ontology module 3 stores an ontology 14 representing the relation among the predicates used to describe the queries in the integrated database system 1 and the predicates correspond to the respective databases of the group of external databases 2. A dictionary module 4 stores a specification description (an external database specification description 15) on the respective external databases of the group of external databases 2. A query acceptance module 5 accepts the query issued by the user or program. A query conversion unit 8 in the query acceptance module 5 converts the accepted query into an internal expression used in the integrated database system 1. A query optimization module 6 refers to the query internal expression generated by the query acceptance module 5 and the ontology 14 stored in the ontology module 3 to generate a set of approximate queries, each of which combines the external databases in the group of external databases 2 to be used, while transforming the internal expression of the query. A query plan generation module 7 generates in a query plan generation unit 12 approximate query plans for the respective approximate queries in the approximate query set generated by the query optimization module 6. The query plan generation module 7 then generates a final query plan by merging the generated approximate query plans in a query plan merging unit 13.

The detailed construction of the respective constitutional elements mentioned above will be described below.

(1) "Ontology Module 3"

Figure 2:
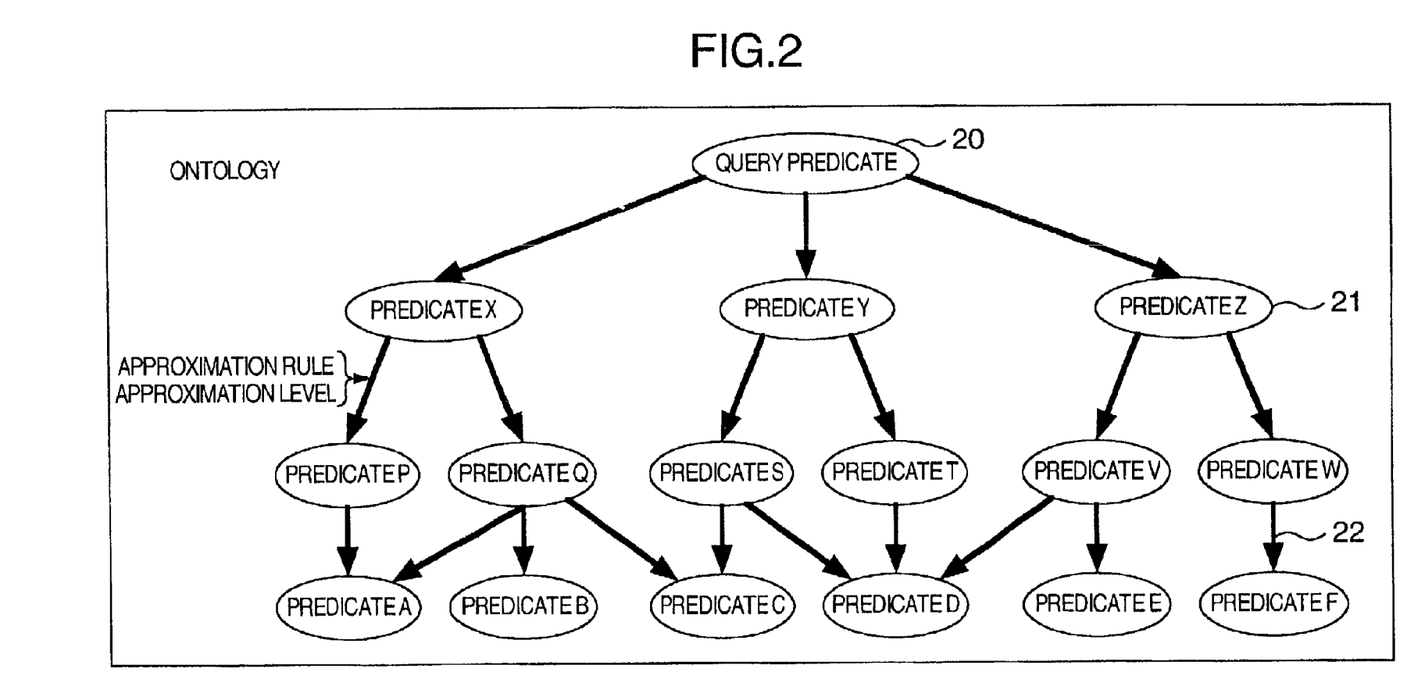
FIG. 2 is a schematic diagram showing an ontology of the embodiment shown in FIG. 1.

The ontology 14 stored in the ontology module 3 is represented by a directed graph as shown in FIG. 2. The ontology 14 is used as a graph structure that classifies the predicates used to describe the queries in the integrated database system 1 and the predicates corresponding to the external databases. Nodes 21 and directed edges 22 of the ontology 14 represent the predicates used as the internal expressions of queries and the relationships among the predicates, respectively. The query issued to the integrated database system 1 is converted into the internal expression, which uses the predicates on the ontology 14, in the query conversion unit 8 of the query acceptance module 5.

In the ontology 14, when the predicate corresponding to node N can be approximated with the combination of the predicates corresponding to other nodes Ni, the edges are extended from the node N to the nodes Ni, respectively. Here, an "approximation rule" and an "approximation level" are set in each of the edges. The approximation rule represents the corresponding relationship when the predicate corresponding to the node N is replaced with the predicate corresponding to each of the nodes Ni. The approximation level represents the degree of connection between the predicates linked together by the approximation rule.

(2) "Group of External Databases 2"

Each of the external databases in the group of external databases 2 comprises the combination of a data source 18 to be queried and a search tool 17 for performing the predetermined query processing on the data source 18.

The dictionary module 4 stores the external database specification description 15 that indicating that data corresponding to which predicates in the ontology 14 are stored in the data source 18, and indicating that the query processing corresponding to which predicates in the ontology 14 can be performed by the search tool 17.

(3) "Dictionary Module 4"

The dictionary module 4 stores a data/query conversion specification description 16 on the correspondence of the data types and the query categories that the integrated database system 1 can convert, as well as the external database specification description 15 on the external databases.

(4) "Query Acceptance Module 5"

The query acceptance module 5 has the query conversion unit 8 that converts the query, which is thrown into the integrated database system 1, into the internal expression which uses the predicates on the ontology 14. For each query issued to the integrated database system 1, it is possible to specify the lower limit of the approximation level and the upper limit of the execution cost when generating the approximate queries, during or before throwing the query into the system.

(5) "Query Optimization Module 6"

The query optimization module 6 includes: an approximate query expansion unit 9 for expanding the thrown-in query into a set of approximate query candidates; an executable query extraction unit 10 for referring to the specification description (external database specification description 15) on the external databases and search tools registered in the dictionary module 4 to extract the executable approximate queries from the set of the expanded approximate query candidates; and an optimum approximate query selection unit 11 for selecting a set of the optimum approximate query candidates (optimum approximate query set) in light of the specified lower limit of the approximation level and the specified upper limit of the execution cost.

(6) "Query Plan Generation Module 7"

The query plan generation module 7 includes: a query plan generation unit 12 for generating an approximate query plan for each approximate query in the optimum approximate query set selected by the query optimization module 6; and a query plan merging unit 13 for merging the approximate query plans for the thrown-in query from the set of the generated approximate query plans according to the appropriate ordering using, for example, the magnitude of the approximation level to generate a set of optimum approximate query plans in terms of the approximation level and the execution cost.

"Overall Flow Chart and Its Explanation"

Figure 3:
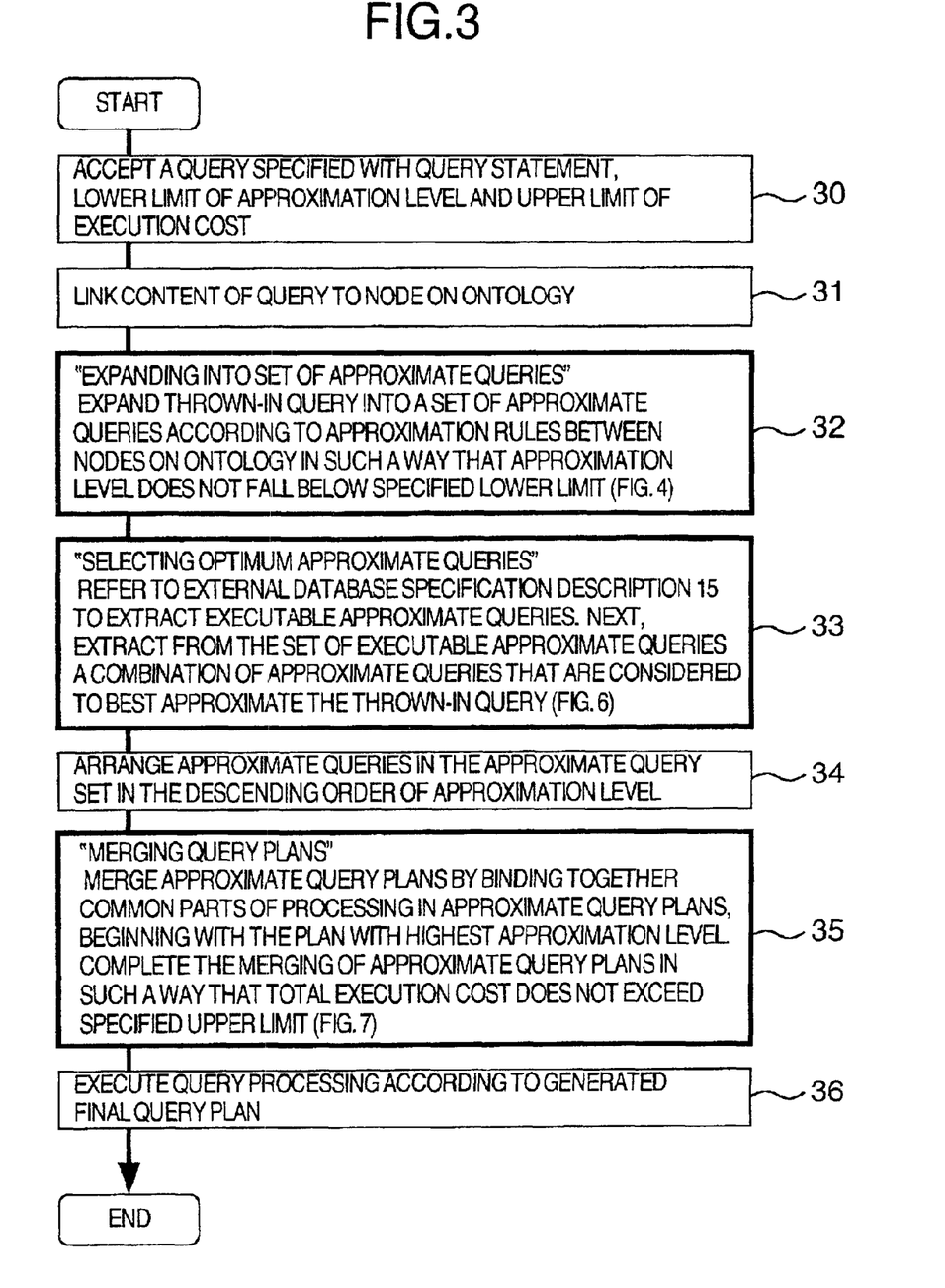
FIG. 3 is a flow chart showing query optimization processing in the embodiment shown in FIG. 1.

Next, referring to FIG. 3, the overall processing flow in the integrated database system 1 according to this embodiment will be described.

The query issued by the user or program to the integrated database system 1 is converted into the internal expression using the predicates on the ontology 14 by the query conversion unit 8 of the query acceptance module 5 (step 31). Here, the lower limit of the approximation level when expanding the thrown-in query into the approximate queries, and the upper limit of the execution cost when generating the approximate query plans may be specified in advance or at the time of issuing the query (step 30).

Next, the query converted into the internal expression is expanded into the set of the approximate queries within the specified lower limit of the approximation level according to the approximation rules set in the nodes on the ontology 14, by the approximate query expansion unit 9 of the query optimization module 6 (step 32).

Then, the executable query extraction unit 10 of the query optimization module 6 refers to the external database specification description 15 to extract only the approximate queries for which the executable approximate query plans can be generated, and leave them in the approximate query set. Further, the optimum approximate query selection unit 11 of the query optimization module 6 selects from the approximate queries in the approximate query set the combination of the approximate queries (the set of the approximate query candidates) that are considered to most appropriately approximate the thrown-in query according to the predetermined criterion. The selected set of the approximate query candidates is left in the approximate query set again (step 33). All of the approximate queries in the approximate query set are arranged in the descending order of their approximation levels (step 34). Then, the selected set of the approximate query candidates are successively merged by the query plan merging unit 13 in such a way that the specified execution cost is not exceeded, while being converted into the approximate query plans by the query plan generation unit 12 of the query plan generation module 7 (step 35). When the final query plan is obtained, it is executed (step 36).

"Flow Chart for Units in Each Module and Its Description"

Next, the processing flow in the units constituting each of the modules will be explained in detail.

Generally, the approximate query in this embodiment is expressed as $\{(n1, \ldots, ni, \ldots, nn), a0\}$. Here, "ni" (i=1, ..., n) represent the predicates on the ontology 14. "a0" represents the approximation level. For the first thrown-in query, it is always expressed as a0=1.0. In the approximate query expressed in this general form, the integrated database system 1 is instructed to return as the query result the set of data satisfying the conditions specified by the predicate n1, ..., the predicate nn. The approximation level a0 means that the returned query result is likely to agree with the query result of the original query at the percentage of about a0.

Figure 4:
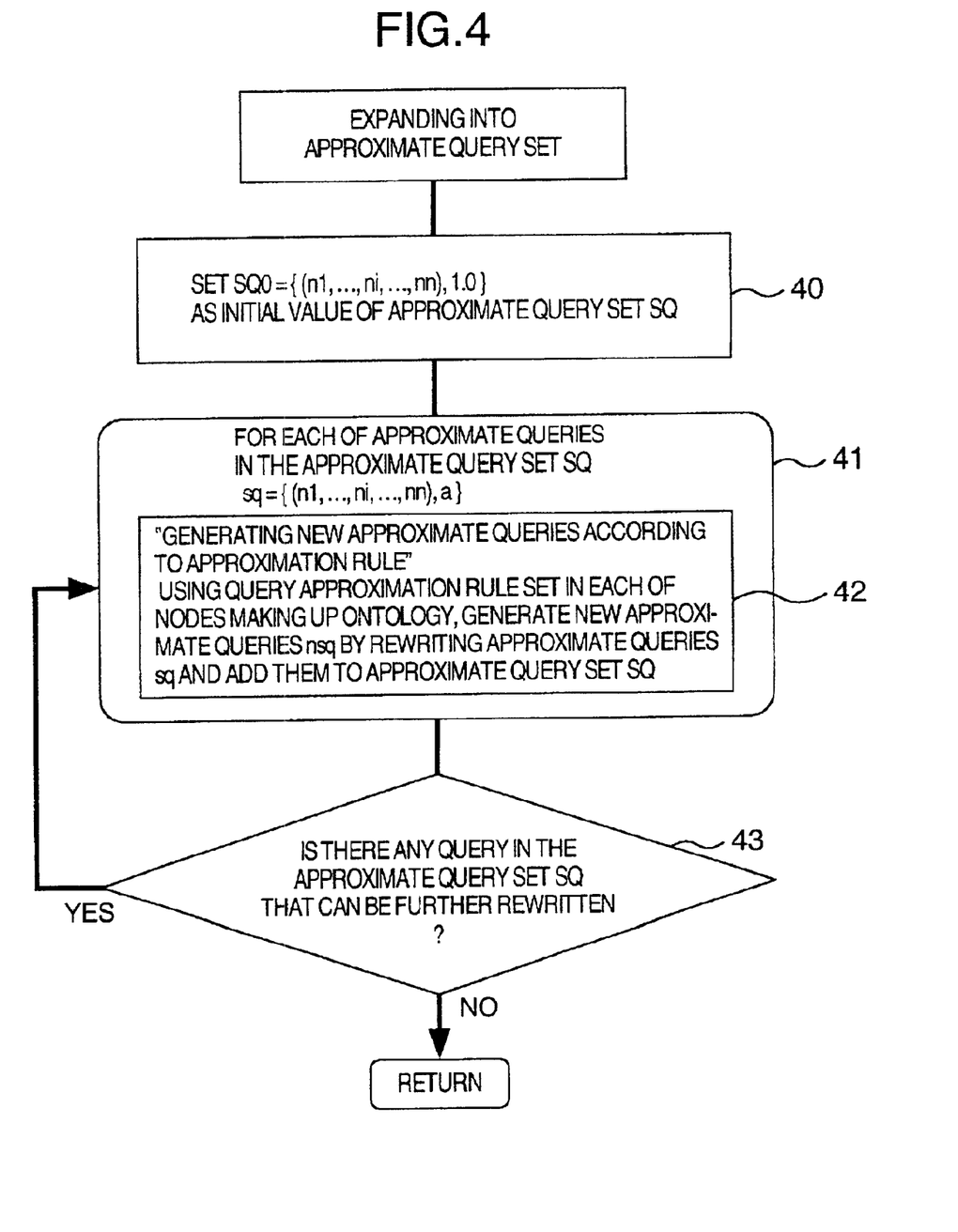
FIG. 4 is a flow chart showing an operation of an approximate query expansion unit in the embodiment shown in FIG. 1.
Figure 5:
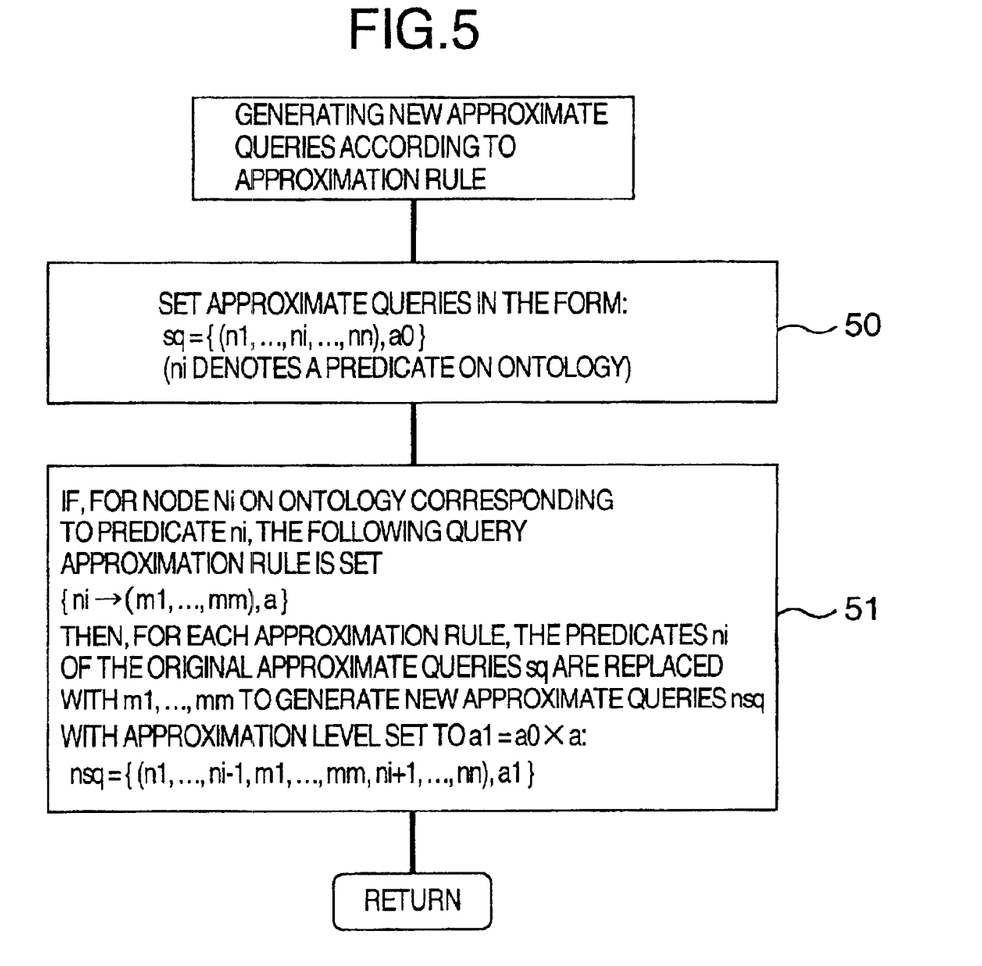
FIG. 5 is a flow chart showing an operation of the approximate query expansion unit.

FIGS. 4 and 5 show the processing flow of the approximate query expansion unit 9 in the query optimization module 6.

In the approximate query expansion in this embodiment, the internal expression $\{(n1, \ldots, ni, \ldots, nn), 1.0\}$ converted from the query, which is thrown from outside into the integrated database system 1, using the predicates on the ontology 14 in the query acceptance module 5, is set as the first element SQ0 in the approximate query set SQ (step 40 in FIG. 4). Then, if the internal expression of each approximate query sq in the approximate query set SQ is assumed to be $\{(n1, \ldots, ni, \ldots, nn), a0\}$ (step 50 in FIG. 5), the following processing is performed on each predicate ni (i=1, ..., n) contained in the approximate query. If the following approximation rule is set for the node Ni on the ontology 14 corresponding to the predicate ni, $\{ni \rightarrow (m1, \ldots, mm), a\}$ then the predicate ni for the original query sq is replaced with "m1 ..., mm" to generate a new approximate query nsq=$\{(n1, \ldots, ni-1, m1, \ldots, mm, ni+1, \ldots, nn), a1\}$ with the approximation level al being set to a0×a (step 51 in FIG. 1).

Then, the generated approximate query nsq is added to the approximate query set SQ (step 42 in FIG. 4).

This operation is repeated until any new approximate query that can be rewritten according to the approximation rule on the ontology 14 no longer exists in the approximate query set SQ (step 43 in FIG. 4). It is noted, however, that when the approximation level of the expanded approximate query is below the specified lower limit, the expanded approximate query may be eliminated from the approximate query set SQ.

Figure 6:
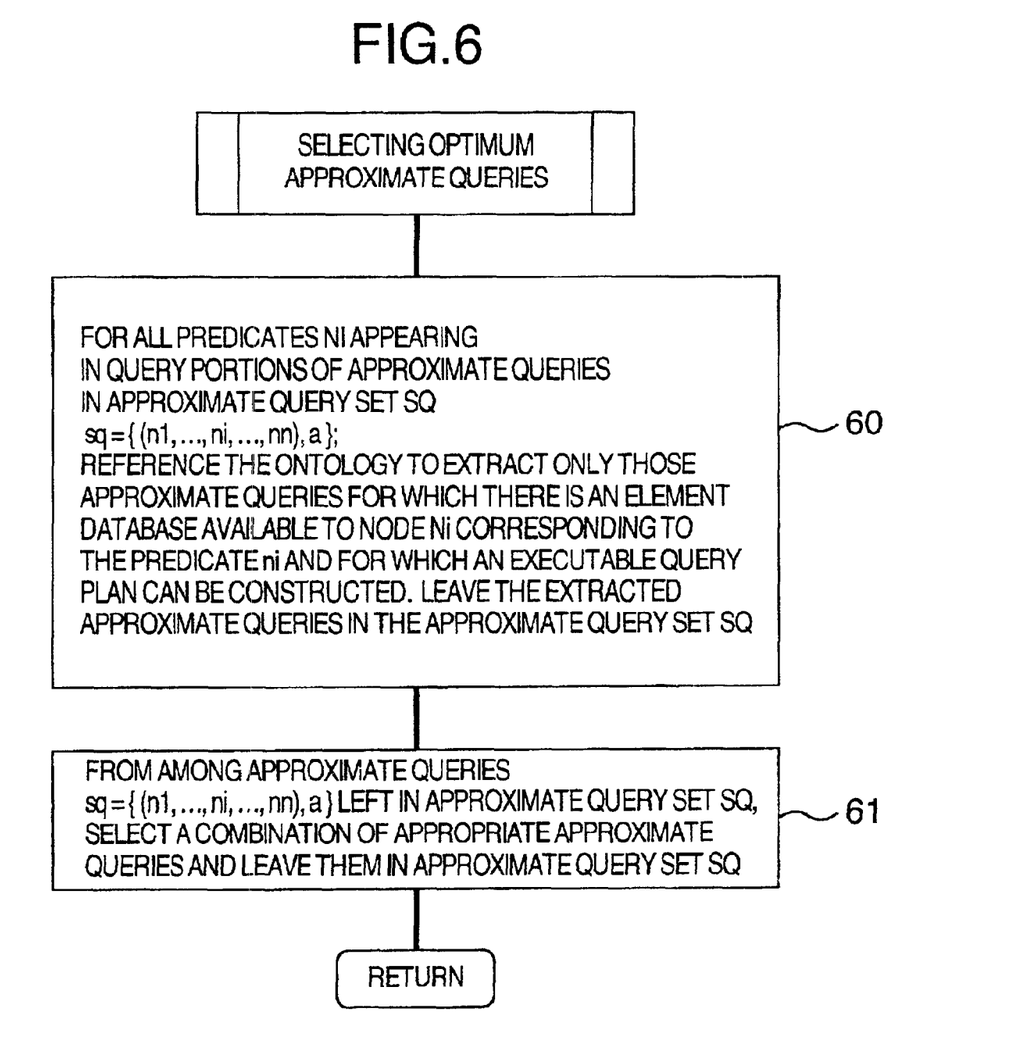
FIG. 6 is a flow chart showing an operation of an executable query extraction unit and an optimum approximate query selection unit.

FIG. 6 shows the processing flow of the executable query extraction unit 10 and the optimum approximate query selection unit 11 in the query optimization module 6.

The executable query extraction unit 10 performs the following processing for all of the approximate queries sq=$\{(n1, \ldots, ni, \ldots, nn), a0\}$ in the approximate query set SQ. For all of the predicates ni appearing in the query portions of the approximate query, the executable query extraction unit 10 refers to the ontology 14 to extract only the approximate queries for each of which there is the available external database corresponding to the node Ni corresponding to the predicate ni, and for each of which the executable query plan can be constructed. The extracted approximate queries are left in the approximate query set SQ (step 60).

The optimum approximate query selection unit 11 selects the combination of the appropriate approximate queries, which efficiently approximate the query result of the original query, from the approximate queries sq=$\{(n1, \ldots, ni, \ldots, nn), a0\}$ remaining in the approximate query set SQ, and leaves the selected combination of the approximate queries in the approximate query set SQ (step 61). As the selection method for the combination of the appropriate approximate queries, it is considered to select the predetermined number of the approximate queries in the descending order of the approximation level, for example. However, the selection method is not limited to any particular method.

Figure 7:
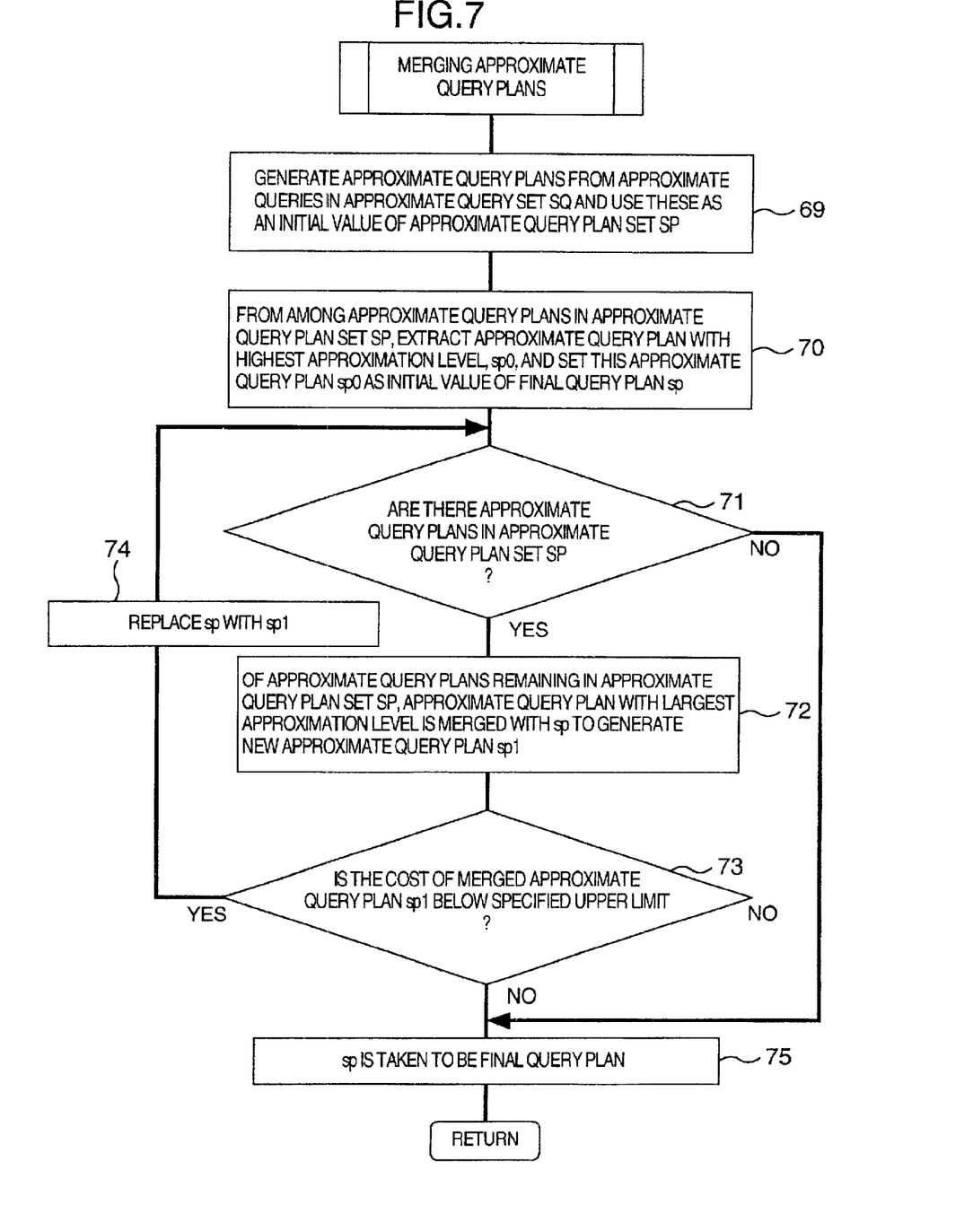
FIG. 7 is a flow chart showing an operation of a query plan generation unit and a query plan merging unit.

FIG. 7 shows the processing flow of the query plan generation unit 12 and the query plan merging unit 13 in the query plan generation module 7.

The query plan generation unit 12 converts the approximate queries in the approximate query set SQ into the approximate query plans which are taken as the initial value of the approximate query plan set SP (step 69). Further, the query plan generation unit 12 extracts the approximate query plan sp0, which has the highest approximation level among the approximate query plans in the approximate query plan set SP, from the approximate query plan set SP. The extracted approximate query plan sp0 is set as the initial value of the final query plan sp (step 70). Then, if there are the approximate query plans remaining in the approximate query plan set SP (step 71), the query plan generation unit 12 extracts the approximate query plans in the descending order of the approximation levels from the approximate query plan set SP. The extracted approximate query plans are merged, for example, by binding the common processing part with the approximate query plan sp to generate the new approximate query plan sp1 (step 72). Here, if the cost of the merged approximate query plan sp1 does not exceed the upper limit of the specified query cost (step 73), the approximate query plan sp is replaced with the merged approximate query plan sp1 (step 74), and the query plan merging operation (steps 71–73) is repeated. Otherwise, the last obtained approximate query plan sp is taken as the final query plan to be executed (step 75).

The optimization scheme described above is only one example, and it is noted that the present invention should not be limited to the case shown above.

"Description of Example Application to Particular Query"

Next, we will explain about an example application of the query optimization processing of this embodiment to a particular query.

Figure 8:
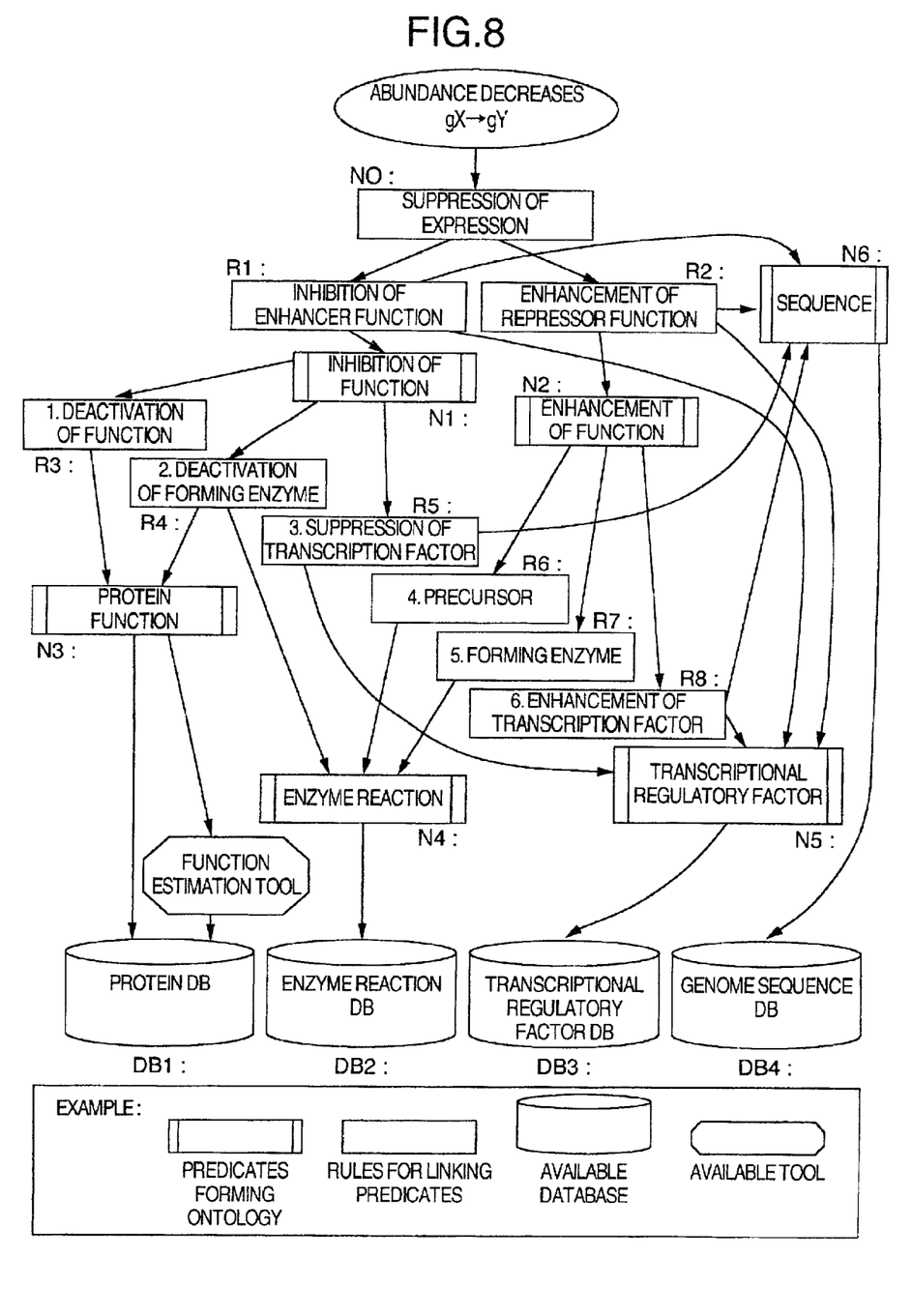
FIG. 8 is an example of an ontology in an integrated database system according to another embodiment of the present invention.

Four external databases DB1–DB4 as shown in FIG. 8 are contemplated as the group of external databases 2 used in the integrated database system 1. That is, the external database DB1 is a protein database that stores information on the amino acid sequences, three-dimensional structures and functions of proteins decoded so far and so forth. The external database DB2 is an enzyme reaction database that stores the various enzyme reaction expressions known so far. The external database DB3 is a transcriptional regulatory factor database that stores information on the transcriptional regulatory factors of genes known so far. The external database DB4 is a genome sequence database that stores information on the genome sequences of various biological species.

The directed-graph structure shown in FIG. 8 is used as the ontology 14 used in the integrated database system 1. The ontology 14 includes seven kinds of predicates (nodes N0–N6), and is set with eight kinds of rules R1–R8 as the approximation conversion rules among the predicates.

That is, the seven kinds of predicates are listed as follows.

(1) Node N0: Suppression of Expression (gene: gX, gene: gY): indicates that gene gX suppresses the abundance of gene gY.

(2) Node N1: Inhibition of Function (protein: pX, protein: pY): indicates that protein pX acts on protein pY to inhibit the function of protein pY.

(3) Node N2: Enhancement of Function (protein: pX, protein: pY): indicates that protein pX acts on protein pY to enhance the function of protein pY.

(4) Node N3: Protein Function (category: X, protein: pX, protein: pY): indicates that protein pX has the function of category X (=Loss of Function and so forth) for protein pY.

(5) Node N4: Enzyme Reaction (protein: pE, protein: pX, protein: pY): indicates that protein pE is an enzyme for catalyzing the reaction from protein pX to protein pY.

(6) Node N5: Transcriptional Regulatory Factor (category: X, protein: pX, gene: gY): indicates that protein pX is the transcriptional regulatory factor of categry X (=enhancer, repressor, and so forth) of gene gY.

(7) Node N6: Sequence (category: X, gene: gX, protein: pX): indicates that gene gX is of category X (=encode and so forth) for protein pX.

As for the approximation rules, the following eight kinds are set.

(1) Rule R1: Inhibition of Enhancer Function={Suppression of Expression (gene: gX, gene: gY)→(Sequence (category: encode, gene: gX, protein: pX), Inhibition of Function (protein: pX, protein: enY), Transcriptional Regulatory Factor (category: enhancer, protein: enY, gene: gY)), 0.5}

(2) Rule R2: Enhancement of Repressor Function= {Suppression of Expression (gene: gX, gene: gY)→ (Sequence (category: encode, gene: gX, protein: pX), Enhancement of Function (protein: pX, protein: reY), Transcriptional Regulatory Factor (category: repressor, protein: reY, gene: gY)), 0.5}

(3) Rule R3: Loss of Function={Inhibition of Function (protein: pX, protein: pY)→(Protein Function (category: deactivation, protein: pX, protein: pY)), 0.7}

(4) Rule R4: Inactivation of Forming Enzyme={Inhibition of Function (protein: pX, protein: pY)→(Protein Function (category: deactivation, protein: pX, protein: pE), Enzyme Reaction (protein: pE, protein: pre-pY, protein: pY), 0.2)

(5) Rule R5: Suppression of Transcription Factor= {Inhibition of Function (protein: pX, protein: pY)→ (Transcriptional Regulatory Factor (category: repressor, protein: pX, gene: g-enY), Sequence (category: encode, gene: g-enY, protein: enY)), 0.1}

(6) Rule R6: Precursor={Enhancement of Function (protein: pX, protein: pY)→(Enzyme Reaction (protein: pE, protein: pX, protein: pY)), 0.3}

(7) Rule R7: Forming Enzyme={Enhancement of Function (protein: pX, protein: pY)→(Enzyme Reaction (protein: pX, protein: pre-pY, protein: pY)), 0.5}

(8) Rule R8: Enhancement of Transcription Factor= {Enhancement of Function (protein: pX, protein: pY)→ (Transcriptional Regulatory Factor (category: enhancer, protein: pX, gene: g-pY), Sequence (category: encode, gene: g-pY, protein: pY)), 0.2}

Figure 9:
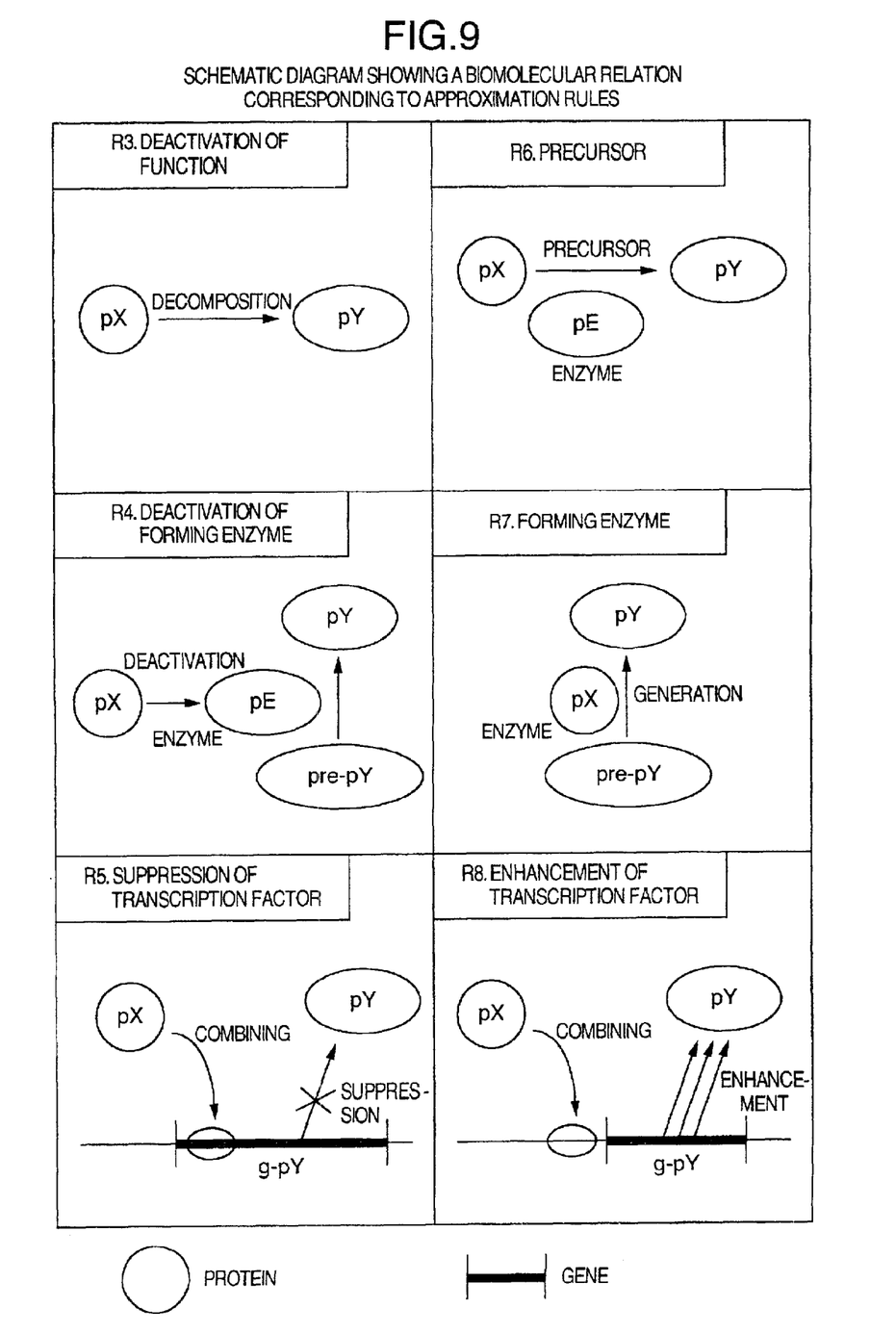
FIG. 9 is a schematic diagram showing a biomolecular relation corresponding to approximation rules in the integrated database system of the other embodiment.

FIG. 9 schematically shows the relation of each factor in the approximation rules R3–R8.

Each of the four external databases DB1–DB4 has the capability to process the query concerning some predicates on the ontology 14, and is associated with the nodes on the ontology 14 corresponding to the predicates. That is, the protein database DB1 can accept the query concerning the predicate "Protein Function", the enzyme reaction database DB2 can accept the query associated with the predicate "Enzyme Reaction", the transcriptional regulatory factor database DB3 can accept the query associated with the predicate "Transcriptional Regulatory Factor", and the genome sequence database DB4 can accept the query associated with the predicate "Sequence".

For example, prior to the experiment which introduces a new gene gX into a cell of a certain living organism, it is assumed that the query "Q=Suppression of Expression (gene: gX, gene: gY)" for obtaining the gene gY expected to be decreased in its abundance due to the introduction of gene gX is issued to the integrated database system 1 together with the specification of the lower limit of the approximation level MINAPPROX=0.1 and the upper limit of the execution cost MAXEXECOST=1000.

Upon accepting this query, the query acceptance module 5 links the thrown-in query to the node N0 representing the corresponding predicate, and converts it into the internal expression S=[P0={N0: Suppression of Expression (gene: gX, gene: gY), 1.0}].

The query optimization module 6 refers to edges E1 and E2 connected to the node N0 to modify the thrown-in query using the associated approximation rules R1 and R2, and adds new approximate queries P1 and P2 to the approximate query set S.

First Application

S=[

P0={N0: Suppression of Expression (gene: gX, gene: gY), 1.0},

P1={N6: Sequence (category: encode, gene: gX, protein: pX),

N1: Inhibition of Function (protein: pX, protein: enY),

N5: Transcriptional Regulatory Factor (category: enhancer, protein: enY, gene: gY), 0.5}, P2={N6: Sequence (category: encode, gene: gX, protein: pX), N2: Enhancement of Function (protein: pX, protein: pre-reY, protein: reY), N5: Transcriptional Regulatory Factor (category: repressor, protein: reY, gene: gY, 0.5)]

The query optimization module 6 expands the thrown-in query into the set of the approximate queries by repetitively applying the above operation to the nodes to which the query is newly corresponded. Here, when the approximation level of the query applied to the node is below the lower limit of the approximation level MINAPPROX, the query is eliminated from the set of the approximate queries, and will not be processed thereafter. Further, when the approximation rule applicable to the predicate appearing in the query no longer exists, the processing of expanding the thrown-in query into the set of the approximate queries is completed.

Second Application

S=[
P0={N0: Suppression of Expression (gene: gX, gene: gY), 1.0},

P1={N6: Sequence (category: encode, gene: gX, protein: pX),

N1: Inhibition of Function (protein: pX, protein: enY),

N5: Transcriptional Regulatory Factor (category: enhancer, protein: enY, gene: gY), 0.5}, P2={N6: Sequence (category: encode, gene: gX, protein: pX), N2: Enhancement of Function (protein: pX, protein: pre-reY, protein: reY), N5: Transcriptional Regulatory Factor (category: repressor, protein: reY, gene: gY, 0.5)]

P3={N6: Sequence (category: encode, gene: gX, protein: pX),

N3: Protein Function (relation: deactivation, protein: pX, protein: enY),

N5: Transcriptional Regulatory Factor (category: enhancer, protein: enY, gene: gY), 0.15}, P4={N6: Sequence (category: encode, gene: gX, protein: pX), N3: Protein Function (relation: deactivation, protein: px, protein: pE), N4: Enzyme Reaction (protein: pE, protein: pre-enY, protein: enY), N5: Transcriptional Regulatory Factor (category: enhancer, protein: enY, gene: gY), 0.05}, P5={N6: Sequence (category: encode, gene: gX, protein: pX), N5: Transcriptional Regulatory Factor (category: repressor, protein: pX, protein: g-enY), N6: Sequence (category: encode, gene: g-enY, protein: enY), N5: Transcriptional Regulatory Factor (category: enhancer, protein: enY, gene: gY), 0.05}, P6={N6: Sequence (category: encode, gene: gX, protein: pX), N4: Enzyme Reaction (protein: pE, protein: pX, protein: reY), N5: Transcriptional Regulatory Factor (category: repressor, protein: reY, gene: gY), 0.15}, P7={N6: Sequence (category: encode, gene: gX, protein: pX), N4: Enzyme Reaction (protein: pX, protein: pre-reY, protein: reY), N5: Transcriptional Regulatory Factor (category: repressor, protein: reY, gene: gY), 0.25}, P8={N6: Sequence (category: encode, gene: gX, protein: pX), N5: Transcriptional Regulatory Factor (category: enhancer, protein: pX, gene: g-reY), N6: Sequence (category: encode, gene: g-reY, protein: reY), N5: Transcriptional Regulatory Factor (category: repressor, protein: reY, gene: gY), 0.1}

Here, when the lower limit of the approximation level is 0.01, all of the above approximate queries are left in the approximate query set S. However, the lower limit of the approximation level specified in this example is 0.1, so that the sixth approximate query P5 shown above is not used. Further, the query plan generation module 7 extracts the executable approximate queries from the set of the approximate queries determined by the query optimization module 6. That is, for a certain approximate query to be executable, the following two conditions must be met.

(1) There is the external database that is available to each of the predicates constituting the approximate queries; and
(2) The query applied to the external database and the search tool can generates the query plan that is executable according to each specification description.

That is, for example, it is assumed that the protein external database DB1 is not available in the above case. Since there is no external database that can be used by the node N3 ("Protein Function"), P0 to P4 of the approximate queries shown above are not executable. Hence, the executable ones of the above approximate queries are P6–P8.

Figure 10:
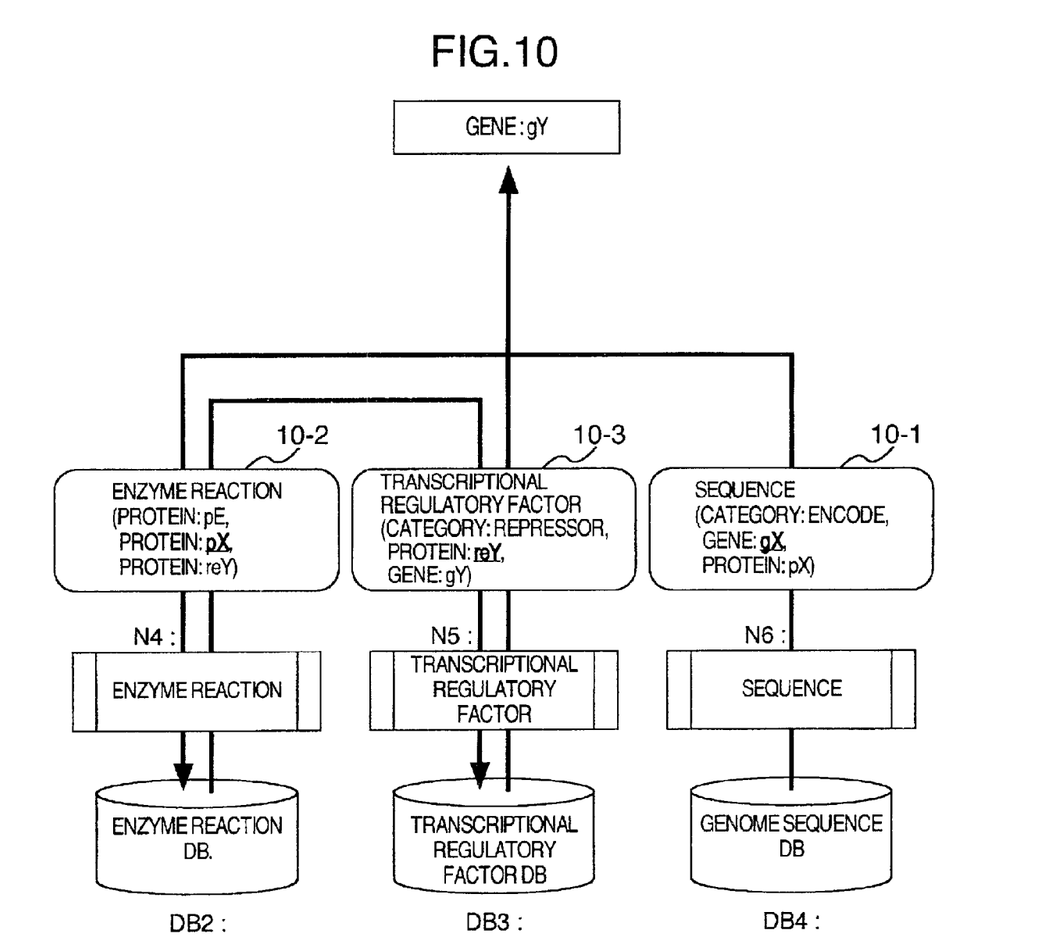
FIG. 10 is an example of an approximate query plan in the integrated database system according to the other embodiment.

For the executable approximate queries P6–P8, the query plan generation module 7 generates the approximate query plans that can be executed by the respective external databases. In the case of the approximate query P6, for example, the approximate query plan as shown in FIG. 10 may be conceived. That is, the query with the gene gX being specified is issued to the genome sequence database DB4 (10-1). The value of the protein pX obtained from the genome sequence database DB4 is used in querying the enzyme reaction database DB2 (10-2). Then, the value of the protein reY obtained from the enzyme reaction database DB2 is used in querying the transcriptional regulatory factor database DB3 (10-3).

Figure 11:
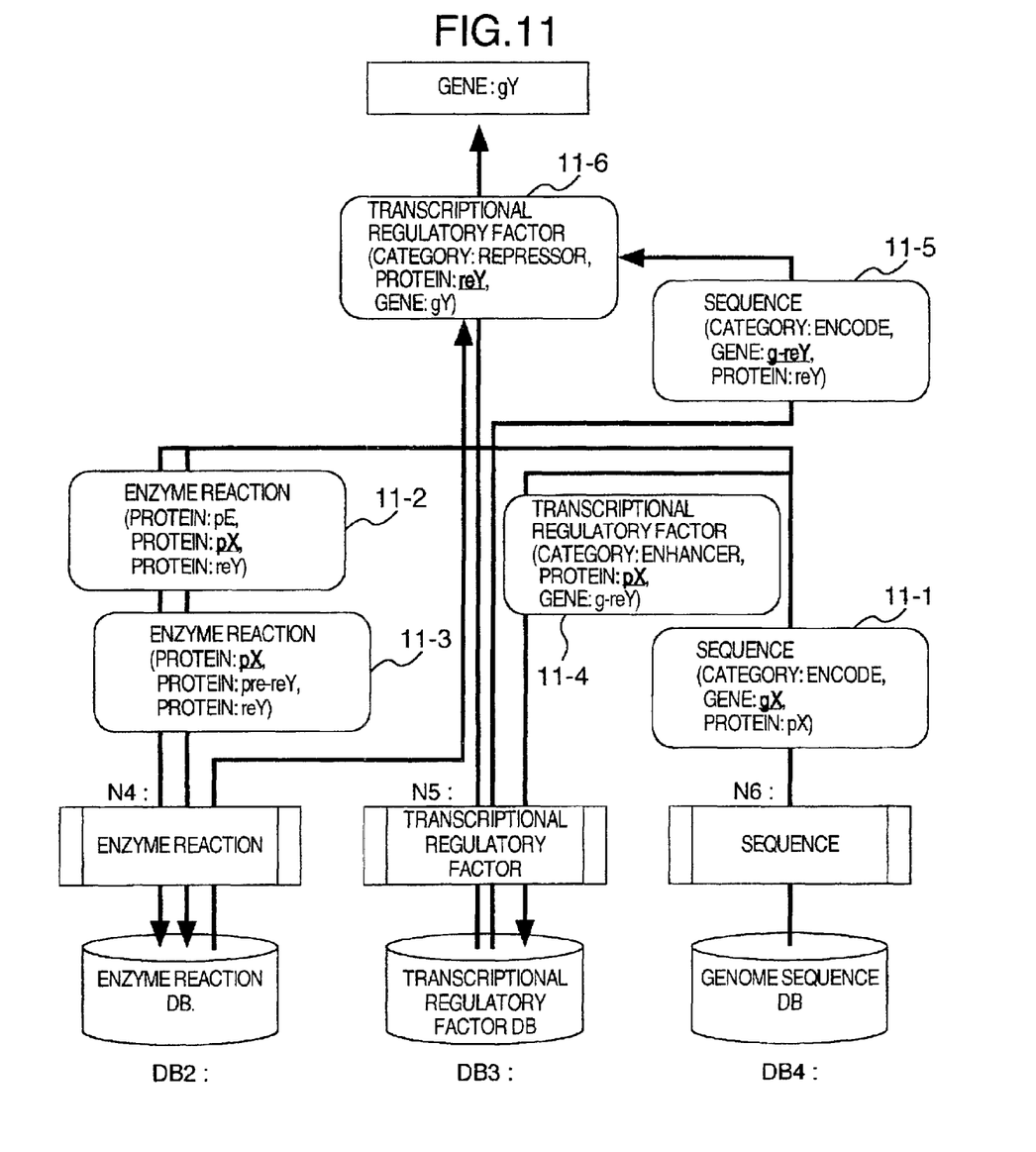
FIG. 11 is an example of a merged approximate query plan in the integrated database system according to the other embodiment.

Next, the query plan generation module 7 attempts to merge the generated approximate query plans in the descending order of the approximation level. In this example, since the query to the genome sequence database DB4 {N6: Encode (gene: gX, protein: pX)} and the query to the transcriptional regulatory factor database DB3 {N5: Repressor (protein: reY, gene: gY)} have common processing, the two queries are merged to generate the approximate query plan as shown in FIG. 11. This approximate query plan issues the query with the gene gX being specified to the genome sequence database DB4 (11-1). Using the value of the protein pX obtained from the genome sequence database DB4, the queries are issued to the enzyme reaction database DB2 and the transcriptional regulatory factor database DB3 (11-2, 3, 4). Using the value of the gene g-reY obtained as the result of querying the transcriptional regulatory factor database DB3, the query is again issued to the genome sequence database DB4 (11-5). Further, using the value of the protein reY obtained as the results of querying the enzyme reaction database DB2 and of last querying the genome sequence database DB4, the further query is issued to the transcriptional regulatory factor database DB3 (11-6). However, it is assumed that the cost of the merged approximate query plan does not exceed the specified upper limit of the query cost.

In the query optimization of the present invention, the predicate forming the thrown-in query is rewritten using the ontology, which is set with weights related to the inter-predicate connection level, to expand the query into a plurality of approximate queries. Some of these approximate queries are merged to be executed. Therefore, it is possible to efficiently retrieve the greater number of query results.

What is claimed is:

1. An integrated database system for performing query processing by combining a plurality of external databases, comprising:

a predicate dictionary including information on connections among predicates having similar meanings and usable in query description of query input into the integrated database system and on strengths of the connections; and query expansion means for referring to the information of connections among predicates having similar meanings and the strength of the connections included in the predicate dictionary to convert a query, which is thrown into the integrated database system, into one or more query sets.

2. An integrated database system according to claim 1, wherein, when the connections among predicates by which the query conversion can be performed exist in the predicate dictionary, the query conversion by the query expansion means referring to the predicate dictionary is repetitively applied.

3. An integrated database system according to claim 1, further comprising:

specification descriptions concerning query processing capabilities of the external databases; and query extraction means, with referring to the specification descriptions, for extracting queries, which can be executed using the external databases, from the converted query set.

4. An integrated database system according to claim 1, further comprising query selection means, with referring to the strengths of the connections, which are set in the predicate dictionary, for selecting an appropriate combination of queries from the converted query set.

5. An integrated database system for performing query processing by combining a plurality of external databases, comprising:

a predicate dictionary including information on connections among predicates used in the query processing and on strengths of the connections; and query expansion means for referring to the connections among predicates and the strength of the connections included in the predicate dictionary to convert a query, which is thrown into the integrated database system, into one or more query sets query selection means for referring to the strengths of the connections, which are set in the predicate dictionary, to select an appropriate combination of queries from the converted query set, wherein, when the query selection means selects queries, a lower limit of a approximation level and an upper limit of an execution cost both of which are specified in advance are referred.

6. An integrated database system according to claim 1, further comprising query plan merging means for generating a query plan by merging the queries in the converted query set.

7. A program storage medium for storing a program which realizes an integrated database system for performing query processing by combining a plurality of external databases, the program storage medium storing:

a predicate dictionary including information on connections among predicates having similar meanings and usable in query description of query input into the integrated database system and on strengths of the connections; and a program for realizing query expansion processing which refers to the predicate dictionary to convert a query, which is thrown into the integrated database system, into one or more query sets.

8. An integrated database system for performing a query processing by combining a plurality of external database comprising:

a predicate dictionary including information on both connections and strengths of the connections between a predicate of a query input into the query processing system and other predicates having similar meaning with the predicate; and query expansion means, with referring to the connections and strengths included in the predicate dictionary, for converting the query into one or more query set usable for the query processing including queries directed to one or more of the plurality of external database.

9. The integrated database system of claim 8, a query conversion performed by the query expansion means is repeated in case that the connections among predicates by which the query conversion can be performed exist in the predicate dictionary.

10. The integrated database system of claim 8, further comprising selecting means for selecting at least one appropriate predicate from the query set converted by the query expansion means.

11. The integrated database system of claim 8, wherein the query expansion means converts the query into the query set with an approximation level defined according to an approximation rule which has been determined in advance.

* * * * *